(12) United States Patent
Filippi et al.

(10) Patent No.: US 10,039,997 B2
(45) Date of Patent: *Aug. 7, 2018

(54) PROCESS AND PLANT FOR DISTILLATION OF METHANOL WITH HEAT RECOVERY

(71) Applicant: Casale SA, Lungano-Besso (CH)

(72) Inventors: Ermanno Filippi, Castagnola (CH); Raffaele Ostuni, Milan (IT)

(73) Assignee: Casale SA, Lugano (CH)

( * ) Notice: Subject to any disclaimer, the term of this patent is extended or adjusted under 35 U.S.C. 154(b) by 727 days.

This patent is subject to a terminal disclaimer.

(21) Appl. No.: 14/374,042

(22) PCT Filed: Nov. 12, 2012

(86) PCT No.: PCT/EP2012/072443
§ 371 (c)(1),
(2) Date: Jul. 23, 2014

(87) PCT Pub. No.: WO2013/110369
PCT Pub. Date: Aug. 1, 2013

(65) Prior Publication Data
US 2015/0202546 A1     Jul. 23, 2015

(30) Foreign Application Priority Data

Jan. 23, 2012  (EP) .................................. 12152187

(51) Int. Cl.
*B01D 3/14*    (2006.01)
*C07C 31/04*   (2006.01)
(Continued)

(52) U.S. Cl.
CPC .............. *B01D 3/14* (2013.01); *B01D 3/002* (2013.01); *B01D 3/007* (2013.01); *B01D 3/146* (2013.01);
(Continued)

(58) Field of Classification Search
CPC ........ B01D 3/007; B01D 3/143; B01D 3/146; C07C 29/80; C07C 31/04
See application file for complete search history.

(56) References Cited

U.S. PATENT DOCUMENTS

| | | | | |
|---|---|---|---|---|
| 2,148,712 A | * | 2/1939 | Reich ..................... | B01D 3/001 159/17.1 |
| 3,259,553 A | * | 7/1966 | Halbritter ................ | B01D 1/26 159/17.2 |

(Continued)

FOREIGN PATENT DOCUMENTS

| | | |
|---|---|---|
| EP | 0210888 A1 | 2/1987 |
| RU | 99352 U1 | 11/2010 |

OTHER PUBLICATIONS

International Search Report issued in connection with PCT/EP2012/072443.

(Continued)

*Primary Examiner* — Jonathan Miller
(74) *Attorney, Agent, or Firm* — Akerman LLP

(57) ABSTRACT

Process and plant for refining a stream of crude methanol (103), comprising: pre-treatment of the crude methanol in a topping stage (100), for the separation of volatile components, at a defined topping pressure (p1); distillation of methanol with at least one final distillation step of methanol at a defined distillation pressure (p4), in which said distillation pressure (p4) is greater than the topping pressure (p1), and in which a gaseous stream of distilled methanol (440), which is produced in the final distillation step, is used to supply at least part of the heat for the pre-treatment topping step.

11 Claims, 2 Drawing Sheets

(51) Int. Cl.
  *C07C 29/80* (2006.01)
  *B01D 3/00* (2006.01)
(52) U.S. Cl.
  CPC .............. *C07C 29/80* (2013.01); *C07C 31/04* (2013.01); *Y02P 70/34* (2015.11)

(56) References Cited

U.S. PATENT DOCUMENTS

| | | |
|---|---|---|
| 4,210,495 A | 7/1980 | Pinto |
| 4,592,806 A | 6/1986 | Ilgner et al. |
| 5,124,004 A * | 6/1992 | Grethlein ............... B01D 3/146 202/154 |
| 5,294,304 A * | 3/1994 | Kano ..................... C07C 29/84 203/19 |
| 2008/0135396 A1 | 6/2008 | Blum |

OTHER PUBLICATIONS

International Preliminary Report on Patentability issued in connection with PCT/EP2012/072443.

* cited by examiner

PROCESS AND PLANT FOR DISTILLATION OF METHANOL WITH HEAT RECOVERY

This application is a national phase of PCT/EP2012/072443, filed Nov. 13, 2012, and claims priority to EP 12152187.6, filed Jan. 23, 2012, the entire contents of both of which are hereby incorporated by reference.

FIELD OF APPLICATION

The present invention refers to a process and plant for distillation of methanol.

PRIOR ART

It is known that the product of plants for synthesising methanol, commonly defined as crude methanol, is an aqueous solution of methanol containing by-products of the synthesis reaction including ethanol, ketones, higher alcohols, and some dissolved gases including mainly $H_2$, $CO$, $CO_2$, $N_2$, $CH_4$.

The crude methanol is distilled to meet the purity specification required on the market. For example, the grade AA specification requires a minimum methanol concentration of 99.85% by weight, and requires that the ethanol does not exceed 10 ppm by weight.

Known distillation processes are based substantially on one or more refining columns. Generally, a refining column is able to separate a light product (for example gas) at the top, and a heavier product (e.g. aqueous solution) at the bottom or tail.

A first process and relative plant, which is widely used, comprises two columns that operate at atmospheric pressure or close to atmospheric pressure. More specifically, said process uses a preliminary treatment column known as topping column or pre-run column and a second distillation column. The first column substantially has the purpose of separating the more volatile components contained in the crude methanol; it receives the crude methanol and separates the light components (light ends) at the top and an aqueous solution at the bottom; the second column carries out the actual distillation, obtaining: refined methanol at the top; a prevalently aqueous stream at the bottom ("bottom water"); a side stream known as "fusel oil" mainly containing water, residual methanol (ca. 1% of the total) and most of the by-products of the synthesis reaction. Said fusel oil has a certain heat value and is usually used as a fuel.

Each column comprises a respective bottom reboiler that heats the bottom of the column and maintains the distillation process. The heat is provided by low-pressure steam, or by a process gas—when available—of suitable thermal level. Moreover, each column requires a top reflux, i.e. part of the distilled methanol is condensed and re-inserted in the top of the column. For this purpose, each column is equipped with a respective top condenser that is normally water or air.

Said configuration with two columns is simple in terms of the plant, but it has the major drawback of consuming a substantial amount of energy both due to the heat supplied to the bottom reboilers, and due to the consumption of cooling water and/or electricity of the top condensers. Moreover, the columns have a relatively large diameter in relation to the production capacity and the plant cost is consequently high.

More specifically, the order of magnitude of the heat consumption of the two bottom reboilers is about 0.8 Gcal per ton of refined methanol. Since the energy consumption necessary to produce a ton of crude methanol is 6-8 Gcal, the order of magnitude of the energy consumption of the distillation is 10% of the total consumption of the plant. The heat to be disposed of in the condensers is comparable with the heat exchanged in the reboilers. In the theoretical case, for example, of removing said heat exclusively with cooling water, the flow rate circulating is relevant, i.e. about 80 m3 per ton of methanol, and consequently there are high costs for pumping, etc.

There are known distillation plants and processes that attempt to at least partially reduce these drawbacks.

U.S. Pat. No. 4,210,495 describes a process with three refining columns, i.e.: a preliminary treatment or topping column and two distillation columns, a column operating at a medium pressure of about 7-8 bar and a final distillation or bottoming column, respectively. The topping and final distillation columns operate substantially at atmospheric pressure or slightly higher pressure (e.g. 1.5 bar). Such a configuration makes it possible to condense the top vapours of the medium pressure column in the bottom reboiler of the final column at atmospheric pressure, recovering heat. However, both the topping column and the intermediate column must be heated and consequently the specific consumption, whilst being lower than a plant with just two columns, is still high.

U.S. Pat. No. 4,592,806 describes an improvement of said process with three columns in which a fourth column treats two lateral streams of fusel oil coming from the two refining columns. Such a solution makes it possible to recover at least part of the methanol contained in the fusel oil that as stated above is about 1-1.5% of the total contained in the crude methanol and therefore is not negligible; however, such an improvement slightly increases the productivity but does not substantially reduce the consumption. In particular the new column also comprises a bottom reboiler and a top condenser that respectively consume heat and cooling water or electricity.

The configurations described above are still widely used. Basically, the processes of the prior art still suffer from a substantial energy consumption of the order of 0.6-0.8 GCal per ton of methanol. There is a continuous incentive to reduce said consumption, as well as to reduce the heat disposed of in the top condensers of distillation columns. Another problem is represented by the size of the equipments (columns) which is proportional to the plant cost.

SUMMARY OF THE INVENTION

The invention has the purpose of reducing the consumption of energy, cooling water and/or electricity in a distillation process of crude methanol comprising a pre-treatment stage, known as topping stage, for the removal of the volatile components, and a bottoming stage.

Such a purpose is accomplished with a process for refining a stream of crude methanol, comprising:
  pre-treatment of said stream of crude methanol in a topping stage, for the separation of volatile components, obtaining a stream of light gases and a solution of de-gassed crude methanol, said pre-treatment being carried out at a defined topping pressure;
  distillation of methanol from said solution of de-gassed crude methanol;
  in which the distillation of methanol comprises at least one final distillation step of methanol from a stream of de-gassed crude methanol, in a final distillation stage and at a defined final distillation pressure, said final distillation pressure being below said distillation pressure, characterised in that:
said bottoming pressure is higher than said topping pressure, and also:
a gaseous stream of distilled methanol produced in the final distillation step at bottoming pressure is used to supply at least part of a heat flow for the pre-treatment topping step.

The process can comprise a single distillation step or many distillation steps in cascade, at decreasing pressures. Said final distillation step is also known as "bottoming" and the respective pressure is known as "bottoming pressure", in particular if the process comprises many distillation steps in cascade.

If there is more than one distillation step, the final distillation (or bottoming) step receives a solution of methanol already partially distilled in the step (or one of the steps) of distillation upstream.

In some embodiments, for example, the distillation of methanol comprises:
at least one distillation step upstream of said final distillation step,
in which a solution of partially distilled methanol, obtained in said at least one distillation step, is directed to the final distillation step,
and in which the pressure or pressures of the distillation step or steps upstream of the final distillation is/are greater than said final pressure.

In other embodiments of the invention the aforementioned final distillation step represents the only distillation step, i.e. the distillation takes place at a single pressure.

In a preferred embodiment the process provides that: a solution containing methanol is taken from a topping stage; said solution is heated through indirect heat exchange with said gaseous stream of distilled methanol coming from a final distillation or bottoming stage; the heated solution is reintroduced in the topping stage, thus obtaining the heating of said topping stage.

Preferably, said gaseous stream of distilled methanol condenses at least partially through the effect of said heat exchange. Preferably, also the solution containing methanol evaporates, in part or entirely, and then goes back to the topping stage in vapour or mixed liquid-vapour phase.

Preferably, the pre-treatment is carried out in a topping column and the final distillation is carried out in a respective column, which can be called a bottoming column. In this case, said gaseous stream of distilled methanol comes from the head of the distillation column and furnishes heat to a solution of methanol taken from the bottom of the topping column; said solution is then reintroduced into the same topping column, after heating and partial or total evaporation.

The heat exchange, in a particularly preferred embodiment, takes place in a condenser/evaporator that acts as a condenser for the final distillation stage and as a heater for the topping stage. Indeed, said exchanger condenses at least part of a gaseous top stream of said distillation stage, and at the same time evaporates a part of bottom solution of the topping stage. Said joint evaporation and condensation step can be carried out in a heat exchanger, for example a tube bundle or plate exchanger, in which the distilled methanol condenses in the hot side, and the solution evaporates in the cold side.

Preferably, the topping pressure is about equal to atmospheric pressure, for example 1-1.5 bar, and the final distillation pressure (bottoming pressure) is at least 2 bar. More advantageously, the topping pressure is in the range 1-1.5 bar and the final distillation pressure is in the range 2-6 bar; more preferably about 5 bar.

It should be noted that the prior art gives an incentive to maintain a final distillation or bottoming pressure as low as possible and typically equal to the topping pressure. The applicant has found that, on the contrary the adoption of a substantially higher bottoming pressure allows an energy saving and makes it possible to optimise the heat flows. Indeed, by increasing the bottoming pressure, the distilled methanol in gaseous state, produced in the bottoming stage, has a substantially higher temperature than the temperature in the topping stage, and sufficient to ensure that a stream of said distilled methanol can be used as a heat source for the preliminary topping step.

Consequently, the invention makes it possible to reduce or eliminate the consumption of heat (for example from condensing steam) for the heating of the topping stage.

Some embodiments comprise a distillation of the degassed methanol, which follows the preliminary topping stage and precedes the bottoming stage. Said distillation can comprise a single pressure level or several pressure levels, according to various embodiments of the invention.

The final bottoming distillation produces distilled methanol in gaseous state, a solution mainly made up of water, and can also produce a side stream represented by the so-called fusel oil. Side streams of fusel oil can also be extracted, if suitable, from the intermediate distillation stages.

The term of gaseous stream of distilled methanol is used to denote the stream resulting from a distillation process, for example taken from the top of a column. Such a stream is mainly made up of methanol, with low content of impurities according to the required specification (e.g. grade AA).

The described pre-treatment (topping) and distillation stages are preferably implemented with respective refining columns. For each stage it is possible to use a single column or many columns in parallel, if necessary.

The object of the invention is also a plant for carrying out the process, according to the attached claims.

Another object of the invention is a method for modifying a distillation plant, in which:
the plant comprises at least one pre-treatment topping stage of crude methanol, for the separation of light components from said crude methanol, at a topping pressure;
the plant comprises at least one stage for the final distillation of methanol from a solution of degassed crude methanol, at a pressure substantially equal to the topping pressure, possibly preceded by other distillation stages at higher pressure;
the modification method comprising:
the final distillation pressure is increased to a value substantially higher than the topping pressure, and
a gaseous stream of distilled methanol produced in the bottoming column is redirected to a heater of the topping stage to supply at least part of a respective heat supply.

The increase in the final distillation pressure, in some cases, can involve the modification or the replacement of a respective distillation column, if the existing column is not suitable for withstanding the increased pressure. Normally, the plant comprises a heater (or reboiler) of the topping column, originally fed by a heat source external to the distillation stage. The method can comprise a modification of the existing heater, for adaptation to operate with the new heat source represented by distilled methanol at higher pressure and temperature, or even the introduction of a new heater. In the latter case, the new heater is preferably a heat exchanger with tubes or plates.

The main advantage of the invention is the energy saving and, consequently, reduction of the production cost of the methanol. Another advantage is the fact that at least part of the gaseous methanol produced in the final distillation or bottoming column can be condensed in the condenser/evaporator that heats the topping column. This eliminates or at least reduces the duty of the top condenser of the bottoming column. In many cases, due to the low availability of cooling water, said top condenser is an air condenser, which is an expensive and large component because it has a low heat exchange coefficient and, consequently, it must have large exchange surfaces; moreover, it consumes electrical energy for the forced circulation of the air itself. The invention makes it possible to condense at least part of the top stream in a plate or tube exchanger, which is more compact and less expensive and does not require forced cooling.

These and other advantages will become clearer with the help of the following description, which illustrates preferred embodiments, not for limiting purposes.

DETAILED DESCRIPTION OF PREFERRED EMBODIMENTS OF THE INVENTION

Figure 1:
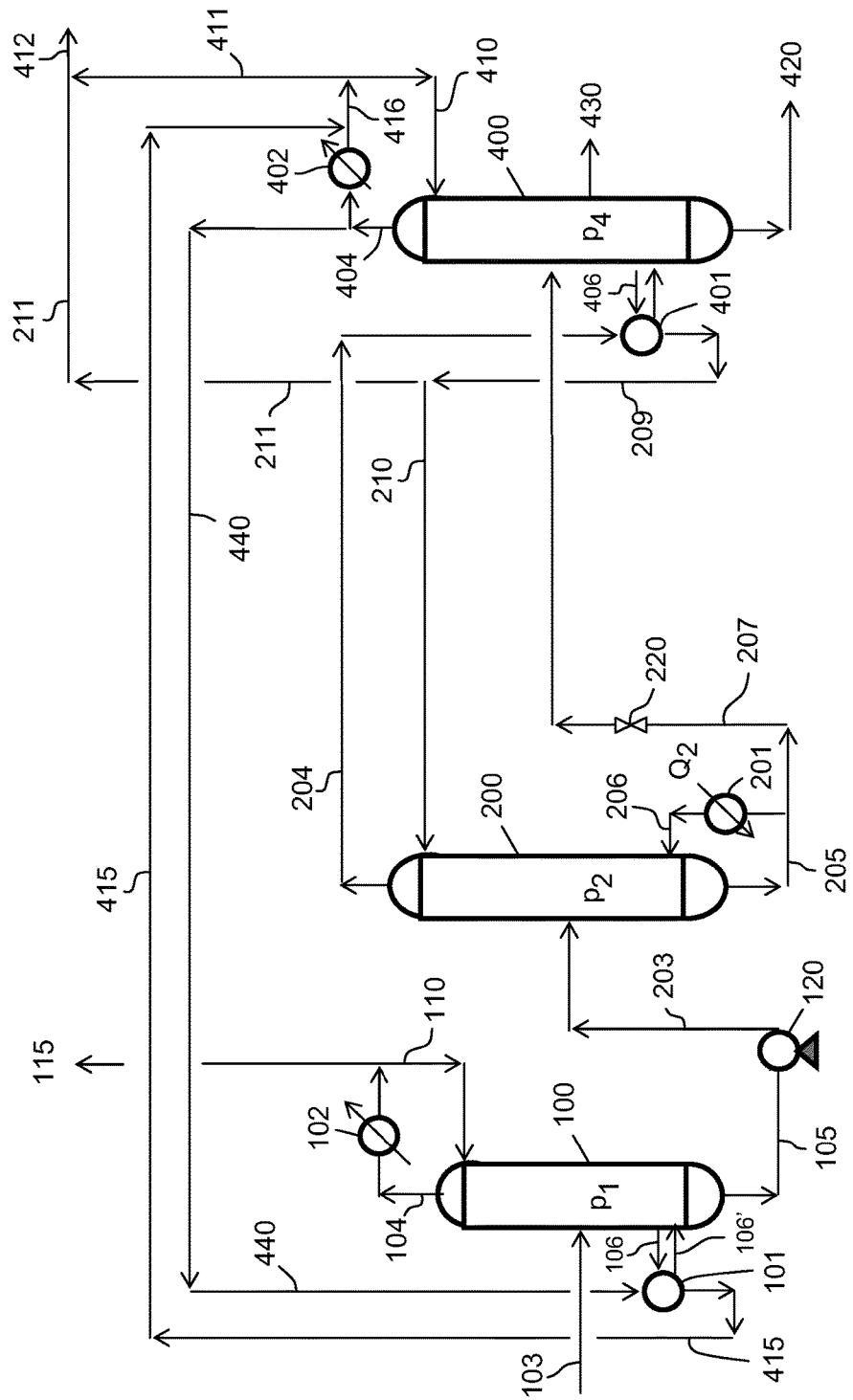
FIG. 1 is a diagram of a distillation section of methanol according to a first embodiment of the invention.

FIG. 1 shows an example embodiment of the invention. In essential terms, it shows a distillation section of crude methanol, comprising a topping column 100, a distillation column 200, and a final distillation column 400.

Said final distillation column 400 is also termed a bottoming column.

The incoming crude methanol is indicated by the stream 103; the outgoing distilled methanol is represented by the stream 412.

The column 100 receives the crude methanol 103 and separates a stream of volatile substances 104 and a stream of degassed methanol 105. Said degassed methanol 105 is sent for distillation in the column 200; a solution 207 leaving said column 200 is further distilled in the bottoming column 400.

The topping column 100 operates at a topping pressure p1, the column 200 operates at a pressure p2 and the bottoming column 400 operates at a bottoming pressure p4.

Said pressure p4 is substantially greater than the topping pressure p1, so that the temperature of the gaseous methanol, distilled in the column 400, is substantially greater than the temperature of the liquid in the bottom of the column 100. Advantageously, the difference is at least 10 celsius degrees, i.e. the temperature of the gaseous methanol at the top of the column 400 is at least 10 degrees higher than the temperature of the liquid in the bottom of the column 100.

As a consequence, at least a part of said gaseous methanol can be used to heat, at least partially, the topping column 100. In the example of FIG. 1, a stream 440 of distilled gaseous methanol, coming from the column 400, provides heat to a solution 106 taken from the bottom (or tail) of the column 100; said solution 106 is then reintroduced (flow 106') after heating and possibly evaporation.

A heat exchanger 101 basically acts as a condenser of the column 400 and as a reboiler of the topping column 100.

Preferably, said reboiler/condenser 101 is represented by a tube bundle exchanger, for example with evaporation of the solution 106 in the shell side and condensation of the distillate 440 in the tube side (or vice-versa). In other embodiments it is possible to use a plated heat exchanger with heat exchange plates housed inside a shell.

The recovery of heat from the stream 440 makes it possible to eliminate, or at least reduce, the addition of external heat for the operation of the column 100. In the example of FIG. 1, all of the heat for the column 100 comes from the condensation of the gaseous methanol 440 and the only input of heat is represented by the heat Q2 for heating the column 200. The energy efficiency of the distillation process is improved.

The process is now described in greater detail, still referring to the preferred embodiment of FIG. 1.

The topping column 100 separates the top gaseous stream 104, which is formed from volatile components lighter than methanol (light ends), and a solution 105 containing methanol. The top stream 104 is condensed in a condenser 102; a part is recirculated as indicated by the line 110 and the remaining part 115 is discharged or removed. The solution 105 is fed through a pump 120 to the next distillation column 200 operating at the pressure p2. It should be noted that said pressure p2 is the maximum pressure of the process, being p2>p4>p1. For example, preferably, the pressure p1 is about 1 bar; the pressure p4 is in the range 2-6 bar; the pressure p2 is at least 8-10 bar or higher.

The distillation column 200 separates a top stream 204 formed from distilled gaseous methanol at the pressure p2, and a bottom solution 205. Part of the bottom solution 205 is heated and evaporated in a reboiler 201, and then reintroduced into the column 200 (line 206). Said reboiler 201 is fed with heat Q2 from an external heat source, like for example steam condensing at a suitable pressure, if available, or other. In some embodiments the source of the heat Q2 can be a process gas.

The remaining part of the bottom solution 205 forms the stream 207 directed to the bottoming column 400. A valve 220 reduces the pressure from p2 to p4. Said bottoming column 400 produces: a stream of distilled gaseous methanol 404; a residual stream 420 essentially made up of water; a stream 430 of so-called fusel oil that can comprise about one percent residual methanol.

The stream 404 of distilled methanol, through the effect of the relatively high pressure of the column 400, has a considerable temperature, typically about 100° C., and it represents the heat source for the reboiler 101 of the topping column. In the example a part 440 of said stream condenses in said reboiler 101, delivering heat to the solution 106 that evaporates at least in part (flow 106') and returns to the base of the column 100. The stream 440 condenses through the effect of the heat exchange, forming liquid methanol 415.

A remaining part of the stream 404 is condensed in the top condenser 402. The methanol 415 coming out from the exchanger 101 is joined with the condensed methanol coming out from said top condenser 402, forming a flow of distilled liquid methanol 416. A part of the methanol (flow 410) returns into the top of the column 400 and the remaining part (flow 411) is removed.

It should be noted that, thanks to the invention, the duty of the condenser 402 is reduced because it must condense only a part of the flow 404. Therefore, the condenser 402 can be smaller and less expensive. This represents an important advantage especially if the condenser is air-cooled and consequently tends to be large in size and expensive.

The figures show a preferred embodiment in which the heat of the distilled gaseous methanol 204 generated in the column 200 is also recovered. The distilled methanol 204 condenses in a heat exchanger 401 heating the bottoming column 400. A solution 406 is taken from the bottom of said column 400, heated and evaporated in the exchanger 401, then reintroduced into the column. The condensed methanol 209 is in part reintroduced into the column 200 (flow 210) and in part removed (flow 211). The flow 211 of methanol, together with the flow 411 coming from the bottoming column, forms the stream 412 of distilled methanol.

The heat exchanger 401 can also be called reboiler/condenser (similarly to the exchanger 101). It represents the bottom reboiler of the column 400 and the top condenser of the column 200.

It should be noted that in the present description the concentrated and distributed pressure drops due to pipes, valves, auxiliary parts, etc. are negliged. The symbols p1, p2, p4 indicate the nominal working pressures of the columns 100, 200, 400; the respective pressures of the top gas and of the liquid extracted at the bottom slightly differ, as is known to a person skilled in the art.

Advantageously, the pressures are also determined as a function of the heat and the temperature level required by the heat exchangers 101 and 401. Preferably, the temperature difference ($\Delta T$) is at least 10° C.: for example the pressure p2 is determined so that the gaseous stream 204 has a temperature of at least 10 degrees higher than the boiling temperature of the solution 406.

The embodiment of FIG. 1 is simplified; other embodiments can comprise further heat recovery provisions. For example, the liquid stream 211 has a relatively high temperature (possibly over 100° C.) and can be used to preheat the solution 203 before entering the column 200, so as to decrease the amount of heat Q2 to maintain the distillation process.

Other embodiments of the invention provide a distillation at many pressure levels between the topping column and the bottoming column. For example, it is possible to install an additional distillation column at intermediate pressure between the pressures p2 and p4, respectively, of the column 200 and of the bottoming column 400.

Figure 2:
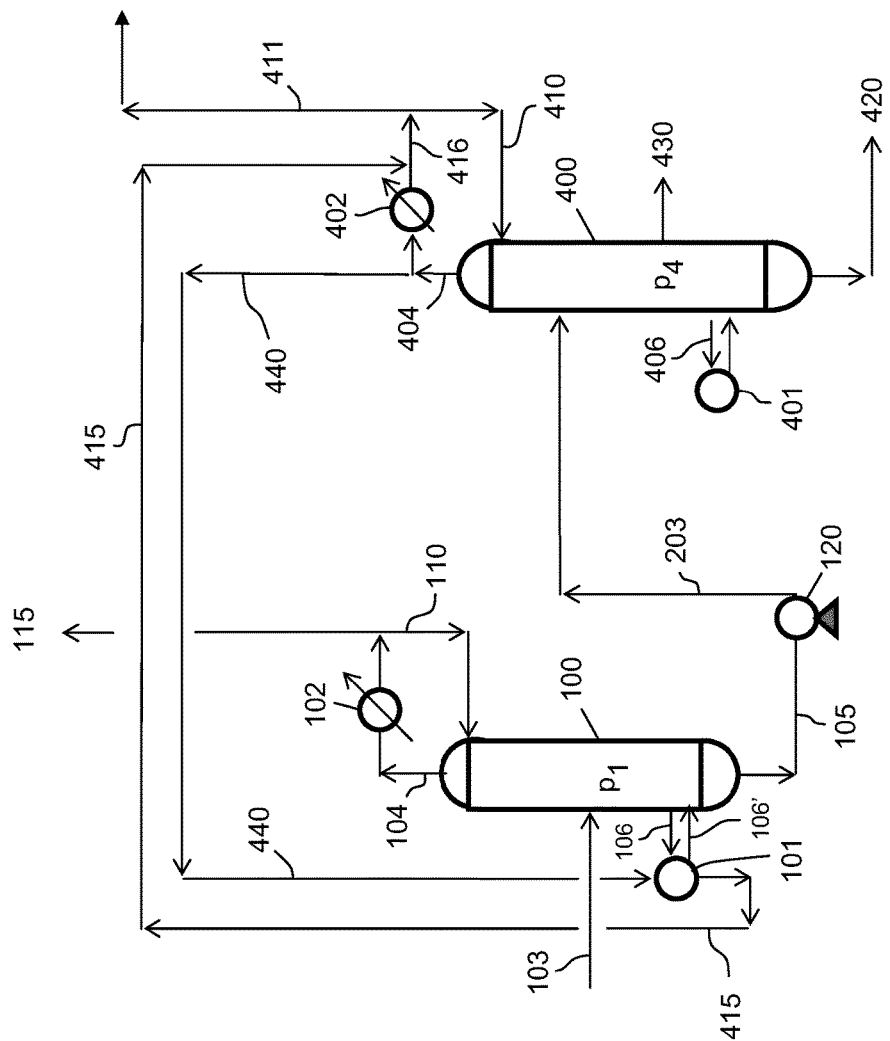
FIG. 2 is a diagram of another embodiment of the invention.

A particularly simplified embodiment is shown in FIG. 2. In said embodiment there is a single distillation stage at pressure p4. The final distillation column 400 represents the only distillation column fed directly with the solution 105 (through pump 120) coming out from the topping column 100. The reboiler 401 is fed with an external heat source, like for example condensing steam or process gas. The stream 411 represents the distilled methanol removed, coming solely from the column 400.

The invention claimed is:

1. A process for refining a stream of crude methanol, comprising:
   pre-treatment of said stream of crude methanol in a topping stage, for the separation of volatile components, obtaining a stream of light gases and a solution of de-gassed crude methanol, said pre-treatment being carried out at a defined topping pressure;
   distillation of methanol from said solution of de-gassed crude methanol in a distillation stage;
   wherein the distillation of methanol stage comprises at least one final distillation step of methanol at a defined distillation pressure, and wherein:
   said distillation pressure of said final step is greater than said topping pressure, and:
   a gaseous stream of distilled methanol produced in the final distillation step, is used to supply at least part of a heat flow for the pre-treatment topping step;
   wherein the distillation of methanol stage further comprises:
   at least one distillation step upstream of said final distillation step,
   wherein a partially distilled methanol solution, obtained in said at least one upstream distillation step, is directed to the final distillation step, and
   wherein the pressure or the pressures of the distillation step(s) upstream of the final distillation step is/are greater than said distillation pressure of said final step.

2. The process according to claim 1, wherein:
   a solution containing methanol is taken from said topping stage;
   said solution is heated by means of indirect heat exchange with said gaseous stream of distilled methanol obtained in the final distillation step;
   the heated solution is re-introduced into the topping stage, thus obtaining the heating of said stage.

3. The process according to claim 2, wherein said gaseous stream of distilled methanol condenses at least partially through the effect of said heat exchange with said solution.

4. The process according to claim 2, wherein said solution containing methanol evaporates at least partially through the effect of said heat exchange.

5. The process according to claim 3, wherein said heat exchange takes place in a tube or plate heat exchanger.

6. The process according to claim 1, wherein the topping pressure is roughly equal to atmospheric pressure and the final distillation pressure is at least 2 bar.

7. The process according to claim 6, wherein the final distillation pressure is comprised in the range 2-6 bar.

8. The process according to claim 1, wherein each of said preliminary topping treatment stage and said distillation stage is carried out in at least one respective distillation column.

9. The process according to claim 1, wherein:
   the gaseous stream of distilled methanol produced in said final distillation step is extracted from the top of a final distillation column in which said final distillation step is carried out;
   a first part of said gaseous stream of distilled methanol is condensed in a condenser-reboiler also operating as a bottom reboiler of a topping column, in which said topping stage is carried out;
   a second part of said gaseous stream of distilled methanol is condensed in a top condenser of said final distillation column;
   said first and second parts are combined to obtain condensed methanol; and
   a part of said condensed methanol is reintroduced into the final distillation column.

10. The process according to claim 1, wherein the topping pressure is not greater than 1.5 bar.

11. The process according to claim 6, wherein the final distillation pressure is about 5 bar.

* * * * *